US008153767B2

(12) United States Patent
Uchigashima et al.

(10) Patent No.: US 8,153,767 B2
(45) Date of Patent: Apr. 10, 2012

(54) ANTIBODY AGAINST AFLATOXINS, SUPPORT USING THE ANTIBODY, METHOD OF IMMUNOLOGICALLY DETECTING AFLATOXINS AND METHOD OF CONCENTRATING AND PURIFYING AFLATOXINS

(75) Inventors: Mikiko Uchigashima, Kyoto (JP); Shiro Miyake, Kyoto (JP); Hiroshi Yamashita, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 262 days.

(21) Appl. No.: 12/515,263

(22) PCT Filed: Nov. 13, 2007

(86) PCT No.: PCT/JP2007/072010
§ 371 (c)(1),
(2), (4) Date: May 15, 2009

(87) PCT Pub. No.: WO2008/059837
PCT Pub. Date: May 22, 2008

(65) Prior Publication Data

US 2010/0062542 A1 Mar. 11, 2010

(30) Foreign Application Priority Data

Nov. 17, 2006 (JP) ................................ 2006-311200

(51) Int. Cl.
*C07K 16/00* (2006.01)
*C12P 21/08* (2006.01)
(52) U.S. Cl. .................. 530/388.9; 530/809; 435/70.21; 435/345

(58) Field of Classification Search ........................ None
See application file for complete search history.

(56) References Cited

U.S. PATENT DOCUMENTS

| | | | |
|---|---|---|---|
| 4,835,100 | A | 5/1989 | Dixon et al. |
| 2009/0269859 | A1 | 10/2009 | Liu |

FOREIGN PATENT DOCUMENTS

| | | | |
|---|---|---|---|
| CA | 1 315 221 | C | 3/1993 |
| CN | 1 588 068 | A | 3/2005 |
| JP | 63219394 | | 9/1988 |
| JP | 04360695 | | 12/1992 |
| JP | 2001187800 | | 7/2001 |
| WO | 2007094945 | A2 | 8/2007 |

OTHER PUBLICATIONS

Zhang et al. Production and characterization of antibodies cross-reactive with major aflatoxins. Experimentia 1989, vol. 45, No. 2, pp. 182-184.*

Holtzapple et al. Characterization of monoclonal antibodies to Aflatoxin M1 and moleculear modeling studies of related aflatoxins. Molecular Immunology 1996, vol. 33, pp. 939-946.*

Candlish, A.A.G. et al., "A Monoclonal Antibody to Aflatoxin $B_1$: Detection of the Mycotoxin by Enzyme Immunoassay", *Letters in Applied Microbiology*, vol. 1, pp. 57-61, 1985.
Groopman, J.D. et al., "High-Affinity Monoclonal Antibodies for Aflatoxins and Their Application to Solid-Phase Immunoassays", *Proc. Natl. Acad. Sci. USA*, vol. 81, pp. 7728-7731, Dec. 1984.
Hertzog, P.J. et al., "Production of Monoclonal Antibodies to Guanine Imidazole Ring-Opened Aflatoxin $B_1$DNA, the Persistent DNA Adduct in vivo", *Carcinogenesis*, 3:7, pp. 825-828, 1982.
Hastings, K.L., et al., "Production and Characterization of a Monoclonal Antibody to Aflatoxin $B_2$", *J. Agric. Food Chem.*, vol. 36, pp. 404-408, 1988.
Candlish, A.A.G. et al., "Aflatoxin monoclonals: academic development to commercial production," Letters in Applied Microbiology, vol. 10, No. 4, pp. 167-170, XP009134507, ISSN: 0266-8254, Published in 1990, Accepted Apr. 14, 1989, 3 pages.
Woychik, Nancy A. et al., "Production and Characterization of Monoclonal Antibodies Against Aflatoxin M1," Applied and Environmental Microbiology, col. 48, No. 6, pp. 1096-1099, XP009134790, ISSN: 0099-2240, Published in Dec. 1984, 4 pages.
Thirumala-Devi, K. et al., "Development and Application of an indirect Competitive Enzyme-Linked Immunoassay for Aflatoxin M1 in Milk and Milk-Based Confectionery," Journal of Agricultural and Food Chemistry, vol. 50, No. 4, pp. 933-937, XP009134497, ISSN: 0021-8561, Published Feb. 13, 2002, Published on Web Jan. 16, 2002, 5 pages.
Groopman, John D. et al., "The Use of Monoclonal Antibody Affinity Columns for Assessing DNA Damage and Repair Following Exposure to Aflatoxin B1," Pharmacology and Therapeutics, vol. 34, No. 2, pp. 321-334, XP025563519, ISSN: 0163-7258, Jan. 1, 1987, 14 pages.
Gathumbi, J.K. et al., "Productin of ultrasensitive antibodies against aflatoxin B1," Letters in Applied Microbiology, vol. 32, No. 5, pp. 349-351, XP009134509, ISSN: 0266-8254, May 2001, 3 pages.
Devi, K.T. et al., "Production and characterization of monoclonal antibodies for aflatoxin B1," Letters in Applied Microbiology, vol. 29, No. 5, pp. 284-288, XP009134508, ISSN: 0266-8254, Nov. 1, 1999, 5 pages.
Haugen Aage et al., "Monoclonal antibody to aflatoxin B1-modified DNA detected by enzyme immunoassay," Proceedings of the National Academy of Science of the United States, vol. 78, No. 7 pp. 4124-4127, XP009134510, ISSN: 0027-8424, Jul. 15, 1981, 4 pages.
Kussak Anders et al., "Determination of Aflatoxicol in Human Urine by Immunoaffinity Column Clean-Up and Liquid Chromatography," Chemosphere, vol. 36, No. 8, pp. 1841-1848, XP009134492, ISSN: 0045-6535, Apr. 8, 1998, 8 pages.

(Continued)

*Primary Examiner* — Shafiqul Haq
(74) *Attorney, Agent, or Firm* — Alleman Hall McCoy Russell & Tuttle LLP (57) ABSTRACT

It is intended to detect, concentrate and purify aflatoxins of all types which are possibly contained in a sample such as a food. It is also intended to detect the total amount or the individual amounts thereof at a high sensitivity. By using aflatoxin B2 or its derivative as a hapten compound, an antibody, which shows the same reactivity to individual aflatoxin analogs and is highly tolerant to organic solvents, is obtained. Then, a detection/concentration/purification means and an immunological detection means with the use of the above antibody are constructed. The detection means thus constructed achieves a high sensitivity and excellent quantification properties.

6 Claims, 3 Drawing Sheets

OTHER PUBLICATIONS

Kussak Anders et al., "Immunoaffinity column clean-up for the high-performance liquid chromatographic determination of aflatoxins B1, B2, G1, G2, M1 and Q1 in urine," Journal of Chromatography B: Biomedical Applications, vol. 672, No. 2, pp. 253-259, XP004043549, ISSN: 0378-4347, Oct. 20, 1995, 7 pages.

Troiano, Roberto et al., "Rapid quantification of aflatoxins in corn by HPLC with kobra cell derivtisation and fluorescence detection," www.chromatographyonline.com, vol. 10, No. 2, XP007913451, <http://las.perkinelmer.com/content/ApplicationNotes/ABR_AflatoxinsInCornByHPLC-KobraCell.pdf>, Jun. 1, 2007, 6 pages.

Uchigashima Mikiko et al., "Development of a Novel Immunoaffinity Column for Aflatoxin Analysis Using an Organic Solvent-Tolerant Monoclonal Antibody," Journal of Agricultural and Food Chemistry, vol. 57, No. 19, pp. 8728-8734, XP009134384, ISSN: 0021-8561, Oct. 19, 2009, 7 pages.

Li, Peiwu et al., "Develpment of a class-specific monoclonal antibody-base ELISA for aflatoxins in peanut," Food Chemistry, vol. 115, No. 1, pp. 313-317, XP025993156, ISSN: 0308-8146, Jul. 1, 2009, 5 pages.

ISA European Patent and Trademark Office, Search Report of EP 07 83 1740, Aug. 23, 2010, Germany, 13 pages.

* cited by examiner

ANTIBODY AGAINST AFLATOXINS, SUPPORT USING THE ANTIBODY, METHOD OF IMMUNOLOGICALLY DETECTING AFLATOXINS AND METHOD OF CONCENTRATING AND PURIFYING AFLATOXINS

TECHNICAL FIELD

The present invention relates to an antibody having novel properties toward aflatoxins or a fragment thereof. The present invention also relates to a support for capturing aflatoxins, an affinity column, a method of immunologically detecting aflatoxins, and a method of concentrating and purifying aflatoxins, which use such an antibody or fragment thereof.

BACKGROUND ART

Aflatoxins that are natural toxins produced by fungi are known as carcinogenetic toxins and can be detected in many foods such as processed goods including peanuts, peanut butter and the like, cereals and processed goods thereof including corn, oats, buckwheat flour and the like, spices including nutmeg, white pepper and the like, and pistachio nuts. Aflatoxins are secondary metabolites produced by filamentous bacteria such as *Aspergillus flavus* and *Aspergillus parasiticus*. Aflatoxin analogs such as B1, B2, G1, G2 are known. Further, a water-soluble aflatoxin metabolite M1, found in milk from cattle having ingested aflatoxins, has been isolated and characterized. It is widely known that among them, aflatoxin B1 when orally ingested exhibits extremely high carcinogenicity.

Structural analogs such as aflatoxins B2, G1, G2 and M1 other than aflatoxin B1, although varying in carcinogenicity more or less depending on animal species and having not so strong toxicity as that of B1, are also recognized to be carcinogenic and acutely toxic in various animals.

In Japan, the concentration of aflatoxin B1 in food is regulated to be 10 ppb or less by the Food Hygiene Law, and peanuts, corn and grains wherein *A. flavus* or aflatoxin B1 are detected with high frequency and which are imported from countries considered as contaminated territory are particularly strictly examined. Because it is necessary that a large number of samples be rapidly dealt with, and a very small amount of aflatoxin be detected, this examination makes use of thin layer chromatography (TLC), an HPLC fluorescence method, and in confirmation examination, an LC/MS method.

When these chemical analysis methods are used, it is necessary that a sample be pulverized and then extracted with an organic solvent, followed by concentrating and purifying its extract. As a concentration and purification means, liquid-liquid partition, silica gel column chromatography and Florisil column chromatography are usually used. Further, because the concentration and purification efficacy of such chromatography is relatively low, antibody affinity column chromatography utilizing the ability of an anti-aflatoxin and the antibody to bind to aflatoxins have come to be used in order to detect a very small amount of contaminating aflatoxins. However, the existing antibody column chromatography is susceptible to some organic solvents, and is thus disadvantageously limited in that only some organic solvents are usable and that said organic solvents may be usable only at low concentrations. Although many antibodies specific to highly toxic aflatoxin B1 have been developed and published, no antibody that also reacts nearly equally to aflatoxins B2, G1, G2, and M1 has been obtained so far. Because aflatoxins B2, G1, G2, and M1 also have toxicities, including carcinogenicity, not only the content of aflatoxin B1 but also the individual contents and total amount of all aflatoxins are often subject to foreign regulations in recent years, and this tendency is estimated to increase from now. However, although there is a great need for monoclonal antibodies against aflatoxins other than B1 type, their study has been less advanced.

By way of example, previously known antibodies against aflatoxin B1 poorly recognize other types of aflatoxins. Further, some monoclonal antibodies recognize aflatoxins B1, B2 and M1 only (for example, Non-Patent Documents 1 and 2). Further still, some monoclonal antibodies recognize highly toxic B1 and G1 only, but do not recognize other types (for example, Patent Document 1). Further still, antibodies formed using B1 as a hapten may be less active toward G1; their ability to bind to G1 may be reduced by several orders of magnitude relative to B1 or B2 (Patent Document 2). On the other hand, there are monoclonal antibodies useful for detection of all aflatoxins (Patent Document 3), but the crossreactivity among aflatoxins B1, B2, G1 and G2, when compared in terms of IC50, varies greatly from 1/5 to 1/10 or less, and thus these monoclonal antibodies when used actually in detection of samples show variation among the aflatoxin analogs.

Meanwhile, a method of quantifying aflatoxin B1 by using a monoclonal antibody against aflatoxin B1 has been studied (Non-Patent Document 3), and detection of aflatoxin B1 has been conducted by ELISA (enzyme-linked immunosorbent assay) etc. However, such a method is also disadvantageous in that since the antibody is susceptible to the organic solvent and reacts poorly with other analogs, the sample must be sufficiently diluted similar to the level of dilution in antibody affinity column chromatography and therefore, depending on the content ratio of aflatoxin analogs in samples, aflatoxin B1 in some samples cannot be accurately quantified.

Patent Document 1: U.S. Pat. No. 4,835,100
Patent Document 2: JP-A 63-219394
Patent Document 3: JP-A 4-360695
Non-Patent Document 1: Candlish J. E. et al., Letters in Appl. Microbiol. 1, 57 (1985)
Non-Patent Document 2: Groopman et al., Proc. Natl. Acad. Sci. USA 81, 7728 (1984)
Non-Patent Document 3: Hertzog P. J. et al., Carcinogenesis 3: pp. 825-828 (1982)

DISCLOSURE OF THE INVENTION

Problems to be Solved by the Invention

As described above, the antibody against aflatoxins, although conventionally required to measure 4 types of oil-soluble aflatoxins and 1 type of metabolite, has a disadvantage that the antibody is susceptible to some organic solvents and does not react equally react to each analog. Further, antibody affinity column chromatography method using such antibodies is also susceptible to some organic solvents and cannot concentrate and purify all the analogs and metabolite equally. Moreover, the immunological measurement methods using such antibodies are disadvantageous in that extracted samples must be sufficiently diluted, and depending on the content ratio of aflatoxin analogs in sample, the aflatoxin analogs in some samples cannot be accurately quantified. Accordingly, there has been demand for a series of methods solving these problems.

Means for Solving the Problems

The present inventors have done extensive studies to provide a detection method in which all types of aflatoxins, that is, aflatoxins B1, B2, G1, G2, and M1 can be equally detected, and even aflatoxins present in infinitesimally small amounts of less than 10 ppb can also be accurately detected, and as a result, have found an antibody or fragment thereof, which has an ability to equally bind to all of these types of aflatoxins and has organic solvent tolerance, as well as a detection method using the same, etc., and have completed the present invention.

That is, the antibody or fragment thereof of the present invention is an antibody or fragment thereof which is obtained by using an antigen derived from aflatoxin B2 or derivative thereof, has an ability to equally bind to all aflatoxins B1, B2, G1, G2, and M1, and has organic solvent tolerance.

In one aspect of the present invention, the derivative of aflatoxin B2 is a compound having a structure represented by the following formula (1):

[Formula 1]

In one aspect of the invention, the antigen derived from the derivative of aflatoxin B2 is a conjugate between the compound of the formula (1) and a high-molecular weight compound.

The antibody described above may be a polyclonal antibody.

The antibody described above may be a monoclonal antibody.

The monoclonal antibody described above is AFB2-3-7F3-3.

The hybridoma of the present invention produces any of the monoclonal antibodies described above.

The hybridoma of the present invention may be a hybridoma which has been deposited internationally under Accession No. FERM ABP-10931 since Nov. 5, 2007, with International Patent Organism Depositary, National Institute of Advanced Industrial Science and Technology, Japan.

The method of immunologically detecting aflatoxins according to the present invention uses all of the antibody or any fragment thereof described above.

The method of immunologically detecting aflatoxins according to the present invention can detect the amount of a single member or a combination of two or more members of aflatoxins B1, B2, G1, G2, and M1, or the total amount of all the members, by using any of the antibody or fragment thereof described above.

In one aspect of the method of immunologically detecting aflatoxins according to the present invention, a solid phase adsorbent is further used.

The support of the present invention includes a solid phase adsorbent and any of the above antibody or fragment thereof immobilized on the solid phase adsorbent.

The solid phase adsorbent described above may be Sepharose.

The affinity column of the present invention includes the support described above.

The method of concentrating and/or purifying aflatoxin in a test sample according to the present invention includes the steps of: preparing a sample which has a possibility of containing aflatoxins; applying the sample onto the affinity column described above; and passing an eluent through the column to recover an eluate and eluting aflatoxin(s) from the antibody or fragment thereof to recover the aflatoxin(s) in the eluate.

The solvent used in the step of applying a sample onto the column may be acetonitrile at a concentration of 1 (v/v) % or more to 20 (v/v) % or less, or methanol at a concentration of 1 (v/v) % or more to 40 (v/v) % or less.

In another aspect of the method of concentrating and/or purifying aflatoxin according to the present invention, the aflatoxin is at least one member selected from the group consisting of B1, B2, G1, G2, and M1.

The method of concentrating and/or purifying aflatoxin according to the present invention includes the step of allowing a sample containing aflatoxin to be captured by the antibody or fragment thereof which has been carried on the support described above, and then eluting the aflatoxin.

In one aspect of the method of concentrating and/or purifying aflatoxin according to the present invention, the aflatoxin is at least one member selected from the group consisting of B1, B2, G1, G2, and M1.

In the method for concentrating and/or purifying aflatoxin according to the present invention, the aflatoxin can also be obtained as the total amount of B1, B2, G1, G2, and M1.

Effect of the Invention

The antibody or fragment thereof of the present invention has an ability to equally bind to all type of aflatoxins and has organic solvent tolerance. In the method of detecting aflatoxins by using this antibody or fragment thereof, therefore, the total amount or the individual contents of all aflatoxins even in minute amounts can be accurately detected simultaneously.

BEST MODE FOR CARRYING OUT THE INVENTION

Hereinafter, the present invention is described in detail.

The "aflatoxin" as the subject in this specification refers to at least one or all of aflatoxins B1, B2, G1, G2, and M1.

Aflatoxin B1 is a compound represented by the following formula:

[Formula 2]

Aflatoxin B2 is a compound represented by the following formula:

[Formula 3]

Aflatoxin G1 is a compound represented by the following formula:

[Formula 4]

Aflatoxin G2 is a compound represented by the following formula:

[Formula 5]

Aflatoxin M1 is a compound represented by the following formula:

[Formula 6]

The phases "has an ability to equally bind" and "reacts equally to" mean that the difference in the reactivity of the antibody or fragment thereof to B1, B2, G1, G2 or M1 is within ±50% relative to its ability (in terms of IC50 (ng/ml)) to bind to B2.

The term "organic solvent tolerance" used in this specification means that in a time point when a test sample is dissolved in an organic solvent and contacted with an affinity matrix, the antibody or fragment thereof is not denatured even when allowed to be present in various kinds of known organic solvents, and particularly means that the antibody or fragment thereof when allowed to be present for at least one hour in 40% methanol or 20% acetonitrile does not change its reactivity to aflatoxins B1, B2, G1, G2, and M1.

When the antibody against aflatoxins is to be produced, aflatoxin B1 having a functional group capable of binding to a protein and having the highest toxicity among the analogs has been generally used as a hapten (immunogen) for immunization. The fact that an antibody showing high reactivity to aflatoxin B1 and having high specificity to aflatoxin B1 can be produced by using a derivative of aflatoxin B1 as an immunogen is well-known.

On the other hand, an antibody showing also high reactivity to other analogs, that is, reacting equally to analog aflatoxins B1, B2, G1, G2 and M1 (which are at least aflatoxin subjects of measurement) could not be obtained by the method of using a derivative of aflatoxin B1 as an immunogen, as shown in the Reference Example. This is possibly because when aflatoxin B1 is used as an immunogen, the presence of a double bond between C-8 and C-9 in aflatoxin B1, that is, the presence of sp2 carbons at positions C-8 and C-9 of the terminal dihydrofuran ring, allows this portion to have a planar structure and simultaneously reduces the distance between the carbons at positions 8 and 9, aflatoxin B1. In contrast, aflatoxin B2, having sp3 carbons at positions 8 and 9, has less steric hindrance so that an antibody having a pocket strongly recognizing this plane dihydrofuran structure is easily produced, and this antibody upon binding to aflatoxin B1 enters the deepest part of the pocket as the binding site of aflatoxin B1 thereby forming a strong bond through which a strong power to recognize aflatoxin B1 is attained. Aflatoxins B2 and G2 having sp3 carbons at positions C-8 and C-9, on the other hand, are more sterically bulky than aflatoxin B1 because of the presence of hydrogen atoms protruding vertically at the positions C-8 and C-9 from the tetrahydrofuran ring plane, and it is thus supposed that the antibody cannot deeply enter this pocket, and consequently shows a significantly lower power to recognize aflatoxins B2 and G2 than aflatoxin B1. Also, aflatoxin M1 has a bulky hydroxyl group at position 9a and it is thus supposed that an antibody is not able to enter this pocket similar to aflatoxins B2 and G2.

Accordingly, a hapten for producing the antibody meeting the objectives of the present invention was designed, and for the following reason, aflatoxin B2 was selected as a candidate for the hapten.

It is estimated that since aflatoxin B2 has a single bond between C-8 and C-9 and has a more sterically bulky structure around the single bond than aflatoxin B1, an antibody recognizing aflatoxin B2 can also recognize aflatoxin B1. (2) Since aflatoxins G1 and G2 are different from aflatoxins B1 and B2 in their structure in only the vicinity of a site for binding to a carrier protein, it is highly possible that the obtained antibodies do not so much recognize the difference therebetween. If this hypothesis is correct, it is considered possible to select, from the obtained antibodies, the antibody reacting equally to aflatoxins B1, B2, G1, and G2, by using techniques of producing monoclonal antibodies. (3) Even if aflatoxin B2 is used as an immunogen, the possibility of obtaining those antibodies having high reactivity to aflatoxin M1 is considered lower than to aflatoxins G1 and G2. However, if aflatoxin B2 is used as an immunogen, the possibility of obtaining those antibodies having a space in which a hydroxyl group of aflatoxin M1 can be accommodated is considered high as compared with aflatoxin B1. Actually, those antibodies obtained with aflatoxin B1 as an immunogen do not always react to aflatoxin M1 but often react to it in a degree as low as few percent. Accordingly, those antibodies having high reactivity to aflatoxin M1 are considered obtainable with a derivative of aflatoxin B2 as an immunogen rather than with a derivative of aflatoxin B1 as an immunogen.

In view of these working hypotheses, aflatoxin B2 was selected as a hapten in producing those antibodies reacting equally to the respective aflatoxin analogs, in order to attempt at producing the antibodies having the objective reactivity by techniques of producing monoclonal antibodies.

As the antigen used in the present invention, which is derived from aflatoxin B2 or derivate thereof, it is possible to conveniently use a conjugate between aflatoxin B2 itself or a compound derived from aflatoxin B2 by various known methods and a high-molecular weight compound.

As used herein, the derivative of aflatoxin B2 refers to a compound in which a wide variety of known functional groups have been introduced into aflatoxin B2 to facilitate binding particularly to a high-molecular weight compound. The derivative of aflatoxin B2 in this specification refers to a compound having the following skeleton into which a functional group was introduced into a carbonyl group at position 1 or 11 of aflatoxin B2.

[Formula 7]

A particularly preferable derivative of aflatoxin B2 is a compound represented by the formula (1) and can be obtained by methods including, but not limited to, a method of converting a ketone group at position 1 of aflatoxin B2 into a carboxymethoxyimino derivative in accordance with a description in Chu, F. S., Hsia, M-T. S., Sun. P., J. Assoc. Off. Anal. Chem. 60, 791 (1977).

The compound obtained by the production method as described above can be subjected as necessary to silica gel chromatography and recrystallization to yield the highly pure objective compound.

The conjugate between the derivative of aflatoxin B2 and a high-molecular weight compound may be produced by methods including, but not limited to, the following method and used as an antigen for immunization.

Preferable examples of the high-molecular weight compound include such as keyhole limpet hemocyanin (KLH), ovalbumin (OVA), bovine serum albumin (BSA), and rabbit serum albumin (RSA).

The binding of the derivative of aflatoxin B2 to the high-molecular weight compound can be achieved by binding a carboxyl group in the derivative to the high-molecular weight compound by methods including, but not limited to, known methods such as an active ester method (A. E. Karu et al.: J. Agric. Food Chem., 42, 301-309 (1994)) and an mixed acid anhydride method (B. F. Erlangeret et al.: J. Biol. Chem., 234, 1090-1094 (1954)).

Further, the derivative of aflatoxin B2 to which a labeling substance such as an enzyme was bound by the same method as described above can be used in an immunological detection method. The labeling substance includes radioisotopes, fluorescence substances and luminescence substances. The radio-isotopes are not particularly limited, and preferable examples include such as [125I], [131I], [3H] and [14C]. The enzymes are not particularly limited and are preferably stable ones having large specific activity, and examples include such as β-galactosidase, β-glucosidase, alkali phosphatase, horseradish peroxidase (referred to hereinafter as "HRP"), and malate dehydrogenase. The fluorescence substances are not particularly limited, and examples include such as fluorescamine and fluorescein isothiocyanate. The luminescence substances are not particularly limited, and examples include such as luminol, luminol derivatives, luciferin and lucigenin.

In the present invention, the conjugate between a derivative of aflatoxin B2 and a high-molecular weight compound can be used as an antigen to produce polyclonal or monoclonal antibodies against aflatoxins.

The polyclonal antibodies can be produced for example by administering the conjugate between a derivative of aflatoxin B2 such as the compound of the formula (1) and a high-molecular weight compound with use of an administration method such as intraperitoneal injection, intravenous injection and subcutaneous injection to the site of each animal where the antibodies can be produced. In administration, Freund's complete adjuvant or Freund's incomplete adjuvant can also be administered in order to enhance the ability of the animal to produce antibodies.

The antigen may be administered only once, but is administered usually once every 2 to 6 weeks and about 2 to 10 times in total. The animals in which the polyclonal antibodies are produced include such as monkeys, rabbits, dogs, guinea pigs, mice, rats, sheep, goats, and chickens.

The titer of the antibody against the antigen of the present invention in serum can be measured by a liquid phase method (for example, a method in which the labeled antigen of the present invention is reacted with antiserum, and then the activity of the label bound to an antibody is measured) or a solid phase method (for example, a method in which the antigen of the present invention has been immobilized on the inner wall of each well in a 96-well plate, then a solution having antiserum diluted appropriately therein is added thereto, an antibody is bound to the antigen, the solution in each well is washed to remove contaminants, and the amount of the antibody bound to the inner wall of each well is measured).

The separation and purification of the polyclonal antibody of the present invention are carried out in accordance with a method of separating and purifying immunoglobulin. This method includes such as salting-out, alcohol precipitation, isoelectric-point precipitation, electrophoresis, absorption and desorption with ion exchangers (for example, DEAE), ultracentrifugation, gel filtration, and specific purification of an antibody by collecting an antibody only with an antigen-bound solid phase or with an active adsorbent such as protein A or protein G and then dissociating the bonding to obtain the antibody. These techniques may be used alone or in suitable combination thereof.

Production of the monoclonal antibody itself can also be carried out according to a usual method (for example, Current Protocol in Molecular Biology, Chapter 11.12-11.13 (2000)). Specifically, a non-human animal such as a rabbit, guinea pig, mouse, rat, sheep or goat is immunized with the conjugate by a conventional method, then the resulting spleen cells are subjected to cell fusion with myeloma cells to prepare hybridoma cells which are then screened, and the resulting monoclonal antibody-producing hybridoma can be cultured to give the monoclonal antibody of the present invention (Current Protocols in Molecular Biology edit. Ausubel et al. (1987) Publish. John Wiley and Sons, Section 11.4-11.11).

The monoclonal antibody-producing hybridoma thus obtained is cultured under predetermined conditions, and while the antibody titer of the produced antibody is measured, the antibody having the desired properties is screened.

The separation and purification of the monoclonal antibody, similar to the polyclonal antibody, are carried out in accordance with the method of separating and purifying immunoglobulin. That is, the method includes such as salting-out, alcohol precipitation, isoelectric-point precipitation, electrophoresis, absorption and desorption with ion exchangers (for example, DEAE), ultracentrifugation, gel filtration, and specific purification of an antibody by collecting an antibody only with an antigen-bound solid phase or with an active adsorbent such as protein A or protein G and then dissociating the bonding to obtain the antibody. These techniques may be used alone or in suitable combination thereof.

A hybridoma producing the monoclonal antibody described above is prepared by conventional methods including, but not limited to, the following method.

An antigen is mixed with an equal volume of adjuvant and then administered intraperitoneally into BALB/c mice. Thereafter, the mouse is subjected periodically to booster immunization. The spleen of a mouse having an increased antibody titer in serum in collected blood is excised, and spleen cells were deprived of tissue fragments etc. in a serum-free DMEM medium (Dulbecco's modified Eagle medium), then transferred to a new medium and suspended completely in the medium. The cells are washed and mixed with mouse myeloma cells. The cells are precipitated to remove the supernatant and subjected to cell fusion under stirring with 50% polyethylene glycol (molecular weight 1500) or the like. After cell fusion, the cells are suspended in HAT medium or the like and cultured under suitable conditions. The activity of antibodies in the culture is examined with ELISA, and cells in a well where the objective antibody has been produced are subjected to limiting dilution, thereby cloning the hybridoma. By cloning, a stable hybridoma strain producing the antibody against aflatoxins is obtained.

The hybridoma of the present invention is cultured in a medium (for example, DMEM containing 10% fetal bovine serum), and a supernatant obtained by centrifuging the culture can be used as a monoclonal antibody solution. The hybridoma can be injected into the peritoneal cavity of the animal from which the hybridoma was derived, to form ascites to be used as a monoclonal antibody solution. The antibody solution can be further purified and concentrated.

In the present invention, the term "fragment" of the antibody refers to an antibody fragment containing an antigen recognition site.

In the present invention, the antibody binding specifically to aflatoxins can be contained to detect aflatoxins easily and used preferably as a kit as a detection means and in a method of detecting aflatoxin as described later. Depending on the detection method, the kit also contains such as a labeled secondary antibody or a labeled hapten compound of aflatoxin, a buffer solution, a detection reagent and/or standard aflatoxin solutions. A preferable kit can be used in ELISA or a detection method using a gold colloid, and when direct competitive ELISA is used, the kit contains such as an antibody against immobilized aflatoxin, a support carrying an antibody, and an enzyme-labeled antigen and a detection reagent.

Further, the present invention relates to a method of detecting aflatoxins, which includes using the antibody or detection means described above. The detection method is not particularly limited as long as it is a method of utilizing a usual antigen-antibody reaction, and examples of such methods include radioimmunoassay (RIA), enzyme immunoassay (EIA), a fluorometric or luminometric detection method, an agglutination method, immunoblotting, immunochromatography, and the like (Meth. Enzymol., 92, 147-523 (1983), Antibodies Vol. II IRL Press Oxford (1989)). The labeling means includes such as enzymes, gold colloids, radioisotopes, fluorescence substances and luminescence substances. The radioisotopes are not particularly limited, and preferable examples include such as [125I], [131I], [3H] and [14C]. The enzymes are not particularly limited and are preferably stable ones having large specific activity, and examples include such as β-galactosidase, β-glucosidase, alkali phosphatase, peroxidase, and malate dehydrogenase. The fluorescence substances are not particularly limited, and examples include such as fluorescamine and fluorescein isothiocyanate. The luminescence substances are not particularly limited, and examples include such as luminol, luminol derivatives, luciferin and lucigenin. Among them, ELISA using β-galactosidase, β-glucosidase, alkali phosphatase, peroxidase, and malate dehydrogenase, or immunochromatography using a gold colloid, is particularly preferable from the viewpoint of sensitivity and ease.

A method of detection by typical ELISA includes such as indirect competitive inhibition ELSA and direct competitive ELISA. For example, aflatoxins can be detected by, for example, direct competitive ELISA using the polyclonal or monoclonal antibody of the present invention as described below.

(1) The polyclonal or monoclonal antibody of the present invention is solid-phased on a support. The support used is preferably a 96-, 48- or 192-well microtiter plate. The antibody may be solid-phased by applying, onto the support, a buffer containing the antibody for immobilization followed by incubation. The concentration of the antibody in the buffer solution is usually from about 0.01 μg/mL to 100 μg/mL. The buffer solution can be a known solution depending on a detection means.

(2) In order to prevent unspecific adsorption of proteins onto the surface of the solid phase support, the surface of the solid phase on which the solid phase antibody was not adsorbed is blocked with a protein or the like irrelevant to the antibody. As the blocking agent, a solution of BSA or skim milk, commercially available Block Ace (manufactured by Dainippon Sumitomo Pharma Co., Ltd.) or the like can be used. Blocking is carried out by adding the blocking agent to the support, incubating it for example at about 4° C. overnight and washing it with a wash fluid. The wash fluid is not particularly limited, and for example, the same buffer solution as (1) above can be used.

(3) Mixtures in which an enzyme-bound hapten prepared by binding an enzyme to a hapten compound of aflatoxin is added to a sample containing aflatoxin at various concentrations are prepared. Preparation of the Enzyme-Bound Hapten is not Particularly Limited and may be conducted by any method as long as it is a method of binding a hapten compound of aflatoxin to an enzyme.

(4) The mixture in the step (3) is reacted with the antibody solid phase support obtained in the step (2) above. By the competitive inhibition reaction between aflatoxin and the enzyme-bound hapten, a conjugate between aflatoxin or the hapten and the solid phase support is formed. The reaction is carried out for example at about 25° C. for about 1 hour. Because aflatoxin is insoluble in water, various organic solvents can be contained in the reaction solution. As the organic solvent, an organic solvent and its content may be selected in the range such that aflatoxins are dissolved therein and the antigen-antibody reaction is not inhibited. Specific examples of the solvent include such as methanol and acetonitrile, and a solvent containing acetonitrile at a concentration of 1 (v/v) % or more to 20 (v/v) % or less, or methanol at a concentration of 1 (v/v) % or more to 40 (v/v) % or less, preferably 1 (v/v) % or more to 30 (v/v) % or less, can be used. After the reaction is terminated, the support is washed with a buffer, and the enzyme-bound hapten not bound to the solid phase antibody is removed. By detecting the amount of the solid phase antibody/enzyme-bound hapten conjugate, the amount of aflatoxins in the sample is determined from a previously prepared calibration curve.

(5) A solution of a coloring substrate for reacting with the support-bound labeled enzyme is added to detect the absorbance of the reaction solution, whereby the amount of aflatoxins can be calculated from the calibration curve. When a peroxidase is used as the labeled enzyme, a coloring substrate solution containing hydrogen peroxide and 3,3',5,5'-tetramethylbenzidine or o-phenylenediamine for example may be used. Usually, the coloring substrate solution is added to the sample, then the mixture is reacted for about 10 minutes at room temperature, and then sulfuric acid is added to terminate the enzyme reaction. When 3,3',5,5'-tetramethylbenzidine is used, the absorbance of the reaction solution at 450 nm is measured. When o-phenylenediamine is used, the absorbance at 492 nm is measured. For correcting the background value, the absorbance at 630 nm is desirably simultaneously measured.

When an alkali phosphatase is used as the labeled enzyme, a method can be included in which p-nitrophenylphosphoric acid for example is colored as a substrate, and a solution of NaOH is added to terminate the enzyme reaction, and the absorbance of the reaction solution at 415 nm is measured.

The reduction rate of the absorbance of the reaction solution in which aflatoxins were added to and reacted with the antibody, relative to the absorbance of the reaction solution to which no aflatoxin was added, is calculated as the inhibition rate. The concentration of aflatoxins in the sample can be determined by using a calibration curve previously prepared from the inhibition rate in the reaction solutions to which known concentrations of aflatoxins were added.

In another aspect, detection of aflatoxins can be carried out by indirect competitive ELISA in the following procedures.

The antigen is solid-phased on a support.

The support used is not particularly limited as long as it is a support used in usual ELISA, and the support is preferably a 96-, 48- or 192-well microtiter plate. The antigen may be solid-phased by applying, onto the support, a buffer containing the solid phase antigen followed by incubation. The concentration of the antigen in the buffer solution is usually from about 0.01 µg/mL to 100 µg/mL. The buffer solution can be a known solution depending on a detection means.

In order to prevent unspecific adsorption of proteins onto the surface of the solid phase support, the surface of the solid phase on which the solid phase antigen was not adsorbed is blocked with a protein or the like irrelevant to the antigen. As the blocking agent, a solution of BSA or skim milk, commercially available Block Ace (manufactured by Dainippon Sumitomo Pharma Co., Ltd.) or the like can be used. Blocking is carried out by adding the blocking agent to the support, incubating it for example at about 4° C. overnight and washing it with a wash fluid. The wash fluid is not particularly limited, and for example, the same buffer solution as (1) above can be used.

An aflatoxin-containing sample and a solution of the polyclonal or monoclonal antibody of the present invention are added to the surface of the solid phase treated in (1) and (2) above, and the antibody is reacted competitively with the solid phase antigen and aflatoxin to form a solid phase antigen/antibody conjugate and an antibody conjugate against aflatoxin. The reaction can be carried out for example at room temperature for about 1 hour. Because aflatoxins are insoluble in water, various organic solvents need to be contained in the reaction solution. As the organic solvent, an organic solvent and its content may be selected in the range such that aflatoxins are dissolved therein and the antigen-antibody reaction is not inhibited. Specific examples of the solvent include such as methanol and acetonitrile, and a solvent containing acetonitrile at a concentration of 1 (v/v) % or more to 20 (v/v) % or less, or methanol at a concentration of 1 (v/v) % or more to 40 (v/v) % or less, preferably 1 (v/v) % or more to 30 (v/v) % or less, can be used.

The amount of the solid phase antigen/antibody conjugate can be detected by adding an enzyme-labeled secondary antibody (for example, an antibody recognizing a mouse antibody). For example, when the mouse monoclonal antibody is used as an antibody against aflatoxin, the antibody against aflatoxin bound to the support is reacted desirably with an anti-mouse goat antibody labeled with an enzyme (for example, peroxidase or alkaline phosphatase). The reaction may be carried out under the same conditions as in (3) above. After the reaction, the support is washed with a buffer solution.

After a solution of a coloring substrate to react with the labeling enzyme of the secondary antibody bound to the support is added, a solution of a coloring substrate to react with the enzyme bound to the secondary antibody is added similarly to the direct competitive ELISA, and the absorbance of the reaction solution is measured, whereby the amount of aflatoxins therein can be determined from a previous prepared calibration curve.

In the detection method of the present invention, a sample can be pretreated depending on the detected substance and then subjected to direct competitive ELISA or indirect competitive ELISA. All methods that can extract aflatoxins can be used for most of the foods. The solvent in the extract is changed to methanol or acetonitrile, and then resulting methanol or acetonitrile solution is diluted with a buffer solution and used as a detection sample. In a simple method, aflatoxins are extracted with methanol or acetonitrile, then diluted with a buffer solution and used directly as sample.

Further, an affinity column carrying the antibody or fragment thereof of the present invention can be used in detection of aflatoxins.

In the present invention, a solid phase adsorbent containing the antibody which binds to all types of aflatoxins and has organic solvent tolerance is used thereby enabling detection of the individual amounts, or the total amount, of aflatoxins contained in the test sample as well as concentration and/or purification of the aflatoxins. Such a method is not particularly limited, and the following method for example can be used.

The purified antibody or fragment thereof of the present invention can be used to produce an affinity matrix material (support) by for example the following method described by Pharmacia Fine Chemicals. The antibody used may be a polyclonal antibody, a monoclonal antibody or a fragment thereof, particularly preferably a monoclonal antibody. In this case, a sufficient amount of the monoclonal antibody is dissolved in a binding buffer solution, pH 8.3, containing NaHCO3 and NaCl, and the resulting antibody solution is added to Sepharose 4B (Sigma) previously activated with cyan bromide by incubation overnight in HCl. After the Sepharose is reacted with the antibody solution, this solid phase adsorbent material is incubated for a suitable time period in, for example, 1.0 Methanolamine, pH 8.5, thereby blocking unbound sites of the antibody-bound gel. An affinity matrix is formed by the monoclonal antibody immobilized on the solid phase adsorbent material and can be used for detection of aflatoxins.

The preferable solid phase adsorbent material includes, but is not limited to, activated Sepharose 4B gel. Other various materials can be used as a solid phase material and examples thereof include other agarose gel compositions, dextran, and carbon and silicon granular preparations including glass plates. Similarly, a method of immobilizing monoclonal antibodies on each of chemical compositions is also known in the art and described in various literatures.

The method of detection, isolation, concentration and/or purification of aflatoxins in a liquid sample in the present invention is exemplified by methods of, but not limited to, affinity chromatography including the following steps. First, a test sample is contacted with the uniform affinity matrix having the polyclonal antibody, the monoclonal antibody or fragment thereof of the present invention immobilized on a solid phase adsorbent material, so that aflatoxins in the test sample are bound to, and supported by, the affinity matrix. The solvent in which the test sample was dissolved includes, but is not limited to, such as acetonitrile and methanol. A solvent containing acetonitrile at a concentration of 1 (v/v) % or more to 20 (v/v) % or less, or methanol at a concentration of 1 (v/v) % or more to 40 (v/v) % or less, preferably 1 (v/v) % or more to 30 (v/v) % or less, can be used. Then, an eluent is added to the affinity matrix in order to release aflatoxins from the polyclonal antibody, the monoclonal antibody or fragment thereof of the present invention. This eluent includes, but is not limited to, such as acetonitrile and methanol. Then, whether aflatoxins are present or not in the eluate recovered from the affinity matrix, and which types of aflatoxins are contained in what amount, can be determined for example by HPLC, etc.

The method of concentration and purification of aflatoxins in a liquid sample according to the present invention is exemplified by methods including, but not limited to, the following method using the polyclonal antibody, the monoclonal antibody or fragment thereof of the present invention. First, a test sample is contacted with the uniform affinity matrix having the polyclonal antibody, the monoclonal antibody or fragment thereof of the present invention immobilized on a solid phase adsorbent material, so that aflatoxins in the test sample are bound to, and supported by, the affinity matrix. Then, contaminants are removed by washing. Then, an eluent is added to the affinity matrix in order to release aflatoxins from the polyclonal antibody, the monoclonal antibody or fragment thereof of the present invention. In this manner, aflatoxins in the liquid sample can be concentrated in an immunologically less contaminated state several thousand times to several ten thousand times higher than the concentration in the original sample. Accordingly, even aflatoxins present in very small amounts in a sample can be concentrated to a much higher degree than in other concentration methods using none of the antibody. In the concentrate so obtained, the content of contaminants or the like interfering with quantification is low. The solvent used in dissolving the test sample to load it onto the affinity matrix includes, but is not limited to, such as acetonitrile and methanol. A solvent containing acetonitrile at a concentration of 1 (v/v) % or more to 20 (v/v) % or less, or methanol at a concentration of 1 (v/v) % or more to 40 (v/v) % or less, preferably 1 (v/v) % or more to 30 (v/v) % or less, can be used.

An important feature of the polyclonal and monoclonal antibody against aflatoxin according to the present invention is that the antibody has a high ability (affinity) to bind not only to aflatoxin B2 antigen but also to B1, G1, G2 and M1 equally. The antibody of the present invention has organic solvent tolerance superior to that of usual existing anti-aflatoxin B1 monoclonal antibodies. Accordingly, the solvent used in dissolving a test sample to contact it with the affinity matrix can be an organic solvent having a relatively high concentration.

Hereinafter, the present invention is described in more detail with reference to the Examples, but these examples are not intended to limit the technical scope of the present invention. Those skilled in the art can easily modify and alter the present invention based on the description of this specification, and such modifications and alterations are contained in the technical scope of the present invention.

Example 1

Synthesis of the Compound (Aflatoxin Hapten) of Formula (1)

8.2 mg (26.1 μmol) of aflatoxin B2 (Wako Pure Chemical Industries, Ltd.) was dissolved in 6.3 ml solution of pyridine:methanol:water (1:4:1), and 10.3 mg (93.9 μmol) of aminooxyacetic acid hemihydrochloride was added thereto and heated under reflux for 2 hours. This reaction mixture was concentrated, and the residues were purified through a silica gel column (chloroform:methanol=9:1) to give aflatoxin B2 hapten, 9.1 mg (yield 90%), in the form of white powder.

The Rf value of the resulting B2 hapten on TLC (silica gel 70F254 plate manufactured by Wako Pure Chemical Industries, Ltd.; developing solvent, chloroform:methanol=9:1) was 0.70 for aflatoxin B2 and 0.54 for the hapten.

Example 2

Preparation of an Immunogen

A conjugate between keyhole limpet hemocyanin (KLH) and the hapten of formula (1) obtained in Example 1 was prepared as an immunogen by the active ester method.

3.3 mg of the aflatoxin B2 hapten produced in Example 1, 2.2 mg of N-hydroxysuccinimide, and 3.7 mg of 1-ethyl-3-(3-dimethylaminopropyl)-carbodiimide hydrochloride were dissolved in 0.5 ml of dimethylsulfoxide, and the resulting solution was stirred for 1.5 hours at room temperature in a dark place to prepare an aflatoxin B2 hapten solution. Separately, 10 mg of KLH was added to 1 ml of 0.1 M borate buffer solution, pH 8.0, and 248 µl of the activated aflatoxin B2 hapten solution was added dropwise thereto and stirred for 1.5 hours at room temperature in a dark place. After the reaction was terminated, the reaction mixture was dialyzed against a physiological phosphate buffer solution (10 mM phosphate buffer solution containing 150 mM NaCl and being adjusted to pH 7.0) at 4° C. for 2 days and then stored at −40° C. Similarly, a conjugate between the aflatoxin hapten and BSA was prepared. The conjugate between the aflatoxin hapten and KLH obtained in this manner was used as an immunogen.

Example 3

Preparation of a Monoclonal Antibody-Producing Hybridoma

The immunogen prepared in Example 2 was dissolved at 2 mg/mL in PBS, mixed with an equal volume of complete adjuvant (trade name: Freund's complete adjuvant; FCA) and then emulsified, and 100 µL of the resulting emulsion was administered intraperitoneally to a 6- to 7-week-old female BALB/c mouse. In a similar manner, 100 µL of 0.5 mg/mL immunogen mixed with an equal volume of incomplete adjuvant (trade name: Freund's incomplete adjuvant: FICA) was administered as booster at 2-week intervals. After immunization was conducted 4 times, blood was collected from eye ground, and it was confirmed by the indirect competitive ELISA that the antibody titer in serum had been sufficiently increased.

Detection of Aflatoxins by the Indirect Competitive ELISA Method

The conjugate between the aflatoxin hapten and BSA obtained in Example 2 was diluted to 1 µg/mL with 10 mM sodium phosphate buffer containing 150 mM NaCl, dispensed in a volume of 100 μL/well into a 96-well microplate and then solid-phased by leaving it overnight at 4° C. Then, the fluid in each well was removed by suction, and then 10 mM sodium phosphate buffer containing 0.4% BSA and 150 mM NaCl and being adjusted to pH 7.0 was dispensed in a volume of 300 μL/well, and each well was blocked by leaving it overnight at 4° C., followed by removing the blocking solution by suction.

(2) 0, 100, 250, 500, 1000, 2500, 5000, and 10000 ng/ml standard solutions of aflatoxins B1, B2, G1, G2 and M1 dissolved in methanol were added at 1% to 10 mM sodium phosphate buffers containing 0.2% BSA and 150 mM NaCl and being adjusted to pH 7.0, to prepare solutions containing each aflatoxin at 0.0, 1.0, 2.5, 5.0, 10, 25, 50 and 100 ng/mL, respectively. Dilution solutions of each aflatoxin were dispensed in a volume of 50 μL/well into the plate on which the conjugate between the aflatoxin hapten and BSA prepared in (1) had been solid-phased. A dilution obtained by diluting the previously obtained antiserum 20,000-fold with 10 mM sodium phosphate buffer containing 0.2% BSA and 150 mM NaCl and being adjusted to pH 7.0 was further added in a volume of 50 μL/well to the plate which was then left at 25° C. for 1 hour and subjected to aflatoxin competitive inhibition reaction.

(3) The conjugate between HRP (horseradish peroxidase) and an anti-mouse IgG sheep antibody (ICN Inc.) was diluted 4000-fold with 10 mM sodium phosphate buffer containing 0.2% BSA and 150 mM NaCl and being adjusted to pH 7.0 to prepare a secondary antibody dilution.

(4) The well reacted in (2) was washed 3 times with 10 mM sodium phosphate buffer containing 150 mM NaCl, and then the secondary antibody dilution was dispensed in a volume of 100 μL/well to the plate and reacted by leaving it at 25° C. for 1 hour.

Each well after being reacted in (4) above was washed 3 times with 10 mM sodium phosphate buffer containing 150 mM NaCl, and 100 μl of a TMB substrate solution (0.1 N sodium acetate solution (pH 5.5) to which 100 μg/mL of 3,3',5,5'-tetramethylbenzidine and 0.006% of hydrogen peroxide had been added) was added to each well and incubated at 25° C. for 10 minutes, and then 100 μL of 1 N sulfuric acid was added to each well to terminate the coloring reaction, and the absorbance at 450 nm was measured with a microplate reader. The results of aflatoxin B2 in this example are shown in FIG. 1.

Confirmation of a Monoclonal Antibody

A mouse having antibody titer increased sufficiently in blood was finally immunized (10 μg/mouse). Three days thereafter, the spleen was excised from the mouse and subjected to cell fusion.

After a superfluous tissue section was removed from the excised spleen in a serum-free DMEM medium (Dulbecco's modified Eagle medium), cells were removed completely from the spleen and suspended in the medium. In order to precipitate suspended large tissue sections, the sample was left for 5 minutes, and the cell suspension was collected in a centrifuge tube and centrifuged at 1500 rpm, and the supernatant was removed by suction, and a fresh serum-free DMEM was added thereto to suspend the cells. This operation was carried out twice.

Previously cultured myeloma cells (P3X63Ag8.653) were recovered, centrifuged to remove the supernatant, and resuspended repeatedly twice in a serum-free DMEM medium.

The respective cells were counted and mixed such that the ratio of the spleen cells to the myeloma cells became 10:1 to 7.5:1, and the mixed cells were centrifuged at 1500 rpm for 5 minutes and the supernatant was removed by suction.

While the centrifuge tube was stirred vigorously, 2 mL of 50% polyethylene glycol (molecular weight 1500) was added over about 60 seconds. Then, about 10 mL of serum-free DMEM was added over 3 to 4 minutes while stirring.

The centrifuge tube was centrifuged at 1000 rpm for 5 minutes to remove the supernatant completely, and the spleen cells were suspended at 2.5×106 cells/mL in HT medium (DMEM medium supplemented with hypoxanthine, thymidine and 10% fetal bovine serum) and dispensed in a volume of 100 μL/well into a 96-well culture plate, and culture was initiated at 37° C. in 8% carbon dioxide gas under humidified conditions.

On the next day, HAT medium (DMEM medium supplemented with hypoxanthine, thymidine, aminopterin, 10% fetal bovine serum) was added in a volume of about 40 μL/well, and the cells were observed until the myeloma cells perished and a colony of the hybridoma cells was formed, and thereafter, HT medium was added while the cells were continuously observed.

Ten days after culture was initiated, the culture was collected, and a well in which the antibody against aflatoxin had been produced was selected by the indirect competitive ELISA method and cultured in an increasing scale in 96 wells, 48 wells and 24 wells sequentially.

Cloning was carried out by limiting dilution in the 24-well stage, and a hybridoma strain producing an AFB2-3-7F3-3 monoclonal antibody against aflatoxin was obtained. The resulting hybridoma strain has been domestically deposited under Accession No. FERM P-21126 with International Patent Organism Depositary, National Institute of Advanced Industrial Science and Technology, Japan. This hybridoma strain has also been internationally deposited under Accession No. FERM ABP-10931 since Nov. 5, 2007, with International Patent Organism Depositary, National Institute of Advanced Industrial Science and Technology.

Hybridoma screening was carried out by using, as an indicator, a reactivity being less than 1 ppb and being exhibited almost equally toward aflatoxins B1, B2, G1 and G2. By further screening hybridomas by using, as an indicator, a reactivity being as high as possible to aflatoxin B1 in the presence of varying concentrations of acetonitrile and methanol, a plurality of antibody-producing cells showing similar reaction characteristics could also be selected besides the AFB2-3-7F3-3 antibody-producing cells.

Example 4

Preparation of a Monoclonal Antibody

The AFB2-3-7F3-3 antibody-producing hybridoma strain obtained in Example 3 was cultured in DMEM containing 10% fetal bovine serum, and about 2×106 cells were injected intraperitoneally to Balb/c female Retire mouse, and then the ascites fluid was collected. The resulting ascites fluid was applied onto a protein G column to purify IgG. The subclass of the obtained monoclonal antibody was IgG1 with λ, chain as light chain.

On the other hand, the AFB2-3-7F3-3 antibody-producing cells were cultured at 37° C. in the presence of 5% CO2 in Dulbecco's MEM medium supplemented with 10% fetal bovine serum, and were confluently proliferated. The cells were centrifuged at 1500 rpm to give the culture supernatant. The culture supernatant was diluted 50-fold with 10 mM sodium phosphate buffer containing 0.2% BSA and 150 mM NaCl and being adjusted to pH 7.0, and then subjected to an indirect competitive ELISA method.

Example 5

Detection of Aflatoxins by an Indirect Competitive ELISA Method

The conjugate between the aflatoxin hapten and BSA obtained in Example 2 was diluted to 1 μg/mL with 10 mM sodium phosphate buffer containing 150 mM NaCl and dispensed in a volume of 100 μL/well into a 96-well microplate and then solid-phased by leaving it overnight at 4° C. Then, the fluid in each well was removed by suction, and then 10 mM sodium phosphate buffer containing 0.4% BSA and 150 mM NaCl and being adjusted to pH 7.0 was dispensed in a volume of 300 μL/well, and each well was blocked by leaving it overnight at 4° C., followed by removing the blocking solution by suction.

0, 10, 25, 50, 100, 250, 500, and 1000 ng/ml standard solutions of aflatoxins B1, B2, G1, G2 and M1 dissolved in methanol were added at 1% to 10 mM sodium phosphate buffers containing 0.2% BSA and 150 mM NaCl and being adjusted to pH 7.0, to prepare solutions containing each aflatoxin at 0.0, 0.1, 0.25, 0.50, 1.0, 2.5, 5.0, and 10.0 ng/ml, respectively. Dilution solutions of each aflatoxin were dispensed in a volume of 50 μL/well into the plate on which the conjugate between the aflatoxin hapten and BSA prepared in (1) had been solid-phased. A dilution obtained by diluting a culture of the monoclonal antibody AFB2-3-7F3-3-producing cells obtained in Example 4, 50-fold with 10 mM sodium phosphate buffer containing 0.2% BSA and 150 mM NaCl and being adjusted to pH 7.0 was further added in a volume of 50 μL/well to the plate which was then left at 25° C. for 1 hour and subjected to aflatoxin competitive inhibition reaction.

Hereinafter, the same procedures as in Example 3 were conducted.

Standard inhibition curves of the monoclonal antibody AFB2-3-7F3-3 solution on aflatoxins B1, B2, G1, G2 and M1 by indirect competitive ELISA are shown in FIG. 2. The IC50 values for all types of aflatoxins were 0.26 for B1, 0.34 for B2, 0.34 for G1, 0.34 for G2, and 0.4 for M1 by indirect competitive ELISA using the monoclonal antibody AFB2-3-7F3-3 solution, and therefore, the reactivity of the antibody to B1, B2, G1, G2 and M1 was within ±50% relative to B2 in term of IC50 values, thus showing equal detection sensitivity among the aflatoxins.

The monoclonal antibodies obtained in other hybridomas obtained in Example 3 were also examined in the same experiment. As a result, the monoclonal antibody AFB2-2-5E10-1 solution for example showed IC50 values for all types of aflatoxins as follows: 0.33 for B1, 0.44 for B2, 0.43 for G1, 0.57 for G2, and 0.55 for M1, and the AFB2-3-4E4-1 solution showed the following IC50 values: 0.3 for B1, 0.44 for B2, 0.43 for G1, 0.53 for G2, and 0.58 for M1.

These values indicate that the antibodies of the present invention have an excellent ability to bind to all of aflatoxins B1, B2, G1, G2 and M1. There are those previously existing monoclonal antibodies against aflatoxins which are induced against B1 as a hapten, but any of such monoclonal antibodies are not those which in comparison with their ability to bind to other types of aflatoxins, "have an ability to equally bind" referred to in this specification. In JP-A 63-219394, for example, it is attempted to obtain antibodies raised against B1 as hapten and specific to B1, and therefore, their ability to bind to G1 is reduced significantly in comparison with their ability to bind to B1 or B2. For example, an antibody referred to in Table 1 as AF-1 has the minimum difference in its binding ability, but nevertheless, its ability to bind to G1 is about 1/10 or less relative to its ability to bind to B1 or B2. On the other hand, there is an example of a produced monoclonal antibody useful for detecting all aflatoxins, but in the Examples in JP-A 4-360695, such a monoclonal antibody showed crossreactivities of 0.44 ng/ml, 2.1 ng/ml, 2.4 ng/ml and 5.2 ng/ml in terms of IC50 for aflatoxins B1, B2, G1 and G2, respectively.

From the foregoing results, it can be seen that analysis of the total amount of all types of aflatoxins and analysis among the aflatoxin analogs become possible with high accuracy by indirect competitive ELISA method using the monoclonal antibody obtained with use of the aflatoxin hapten compound of the present invention.

Example 6

Methanol Tolerance of the Antibody

The methanol tolerance of the monoclonal antibody AFB2-3-7F3-3 was examined. 0%, 20%, 40%, 60%, 80% and 100% aqueous methanol solutions were prepared, and each aqueous methanol solution was mixed at a ratio of 19/1 with 10 mM sodium phosphate buffer containing 0.2% BSA and 150 mM NaCl and being adjusted to pH 7.0, and further 0, 10, 25, 50, 100, 250, 500 and 1000 ng/ml standard solutions of aflatoxin B2 were added at 1% to the aqueous methanol solutions each having the predetermined concentration, to prepare solutions containing aflatoxin B2 at a concentration of 0, 0.1, 0.25, 0.5, 1.0, 2.5, 5.0 and 10.0 ng/mL, respectively. The solution containing methanol at each concentration and aflatoxin B2 at each concentration was added in a volume of 50 μL/well to the plate on which the conjugate between the aflatoxin hapten and BSA prepared in (1) in Example 3 had been solid-phased.

Figure 1:
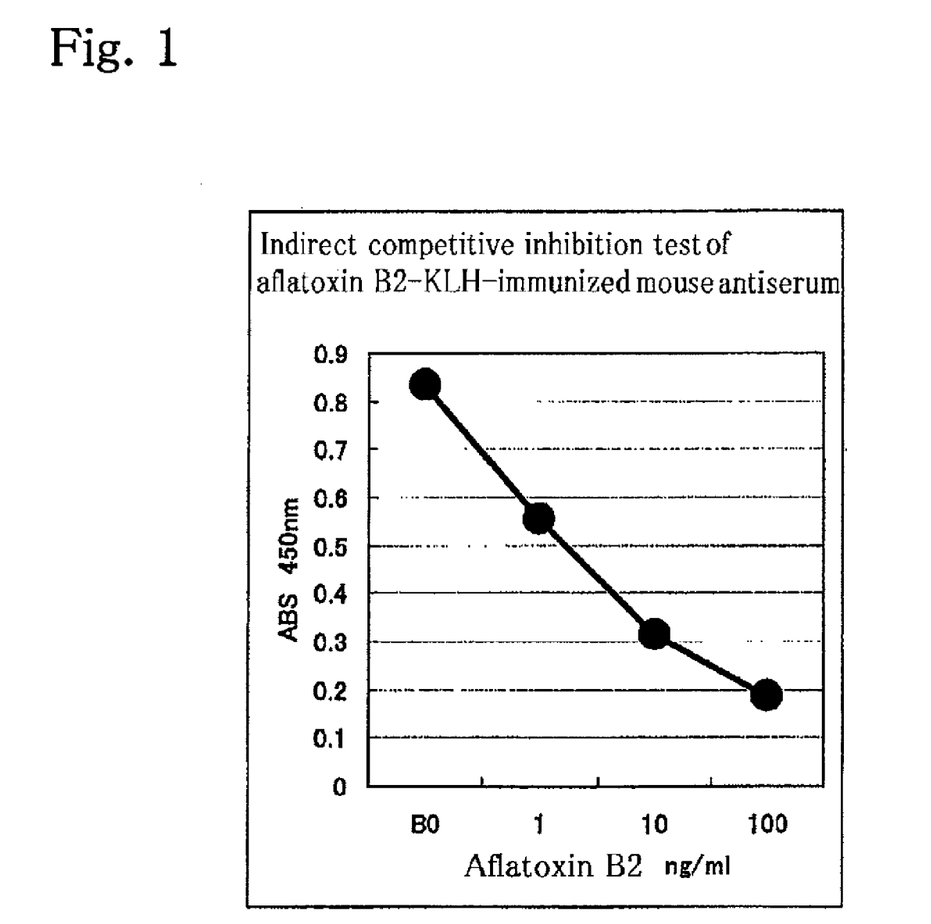
FIG. 1 shows an inhibition curve of aflatoxin B2-KLH-immunized mouse antiserum on aflatoxin B2 in indirect competitive ELISA.
Figure 2:
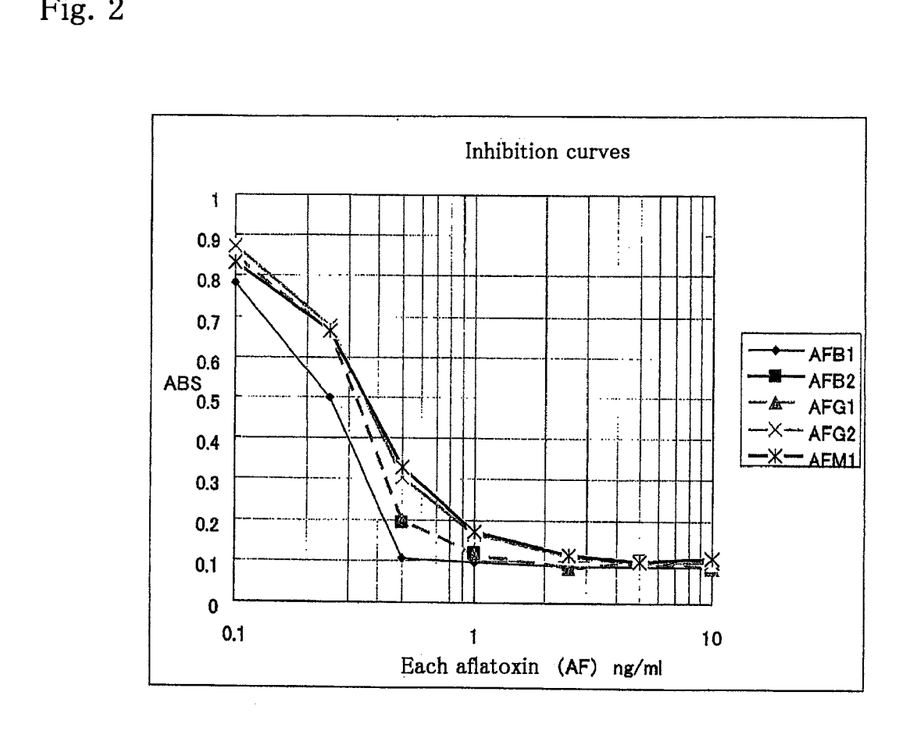
FIG. 2 shows inhibition curves of the antibody (AFB2-3-7F3-3) on aflatoxins in direct competitive ELISA.
Figure 3:
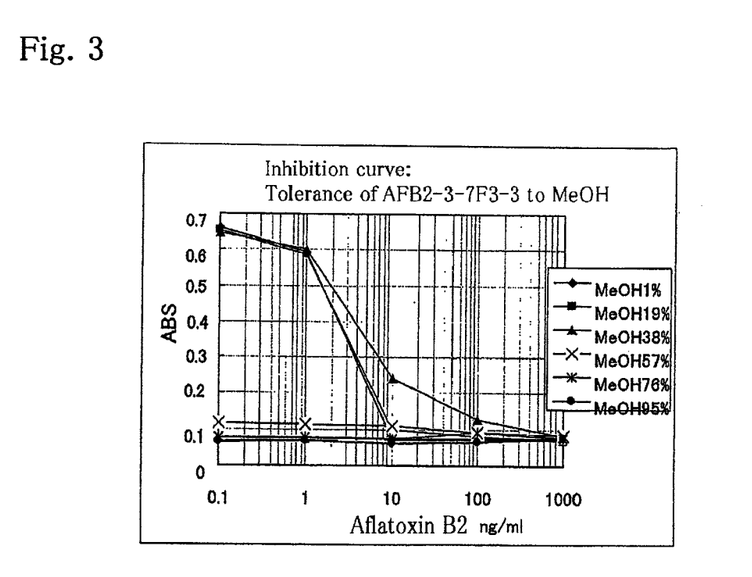
FIG. 3 shows inhibition curves of the antibody (AFB2-3-7F3-3) on aflatoxin B2 in the presence of methanol in direct competitive ELISA.
Figure 4:
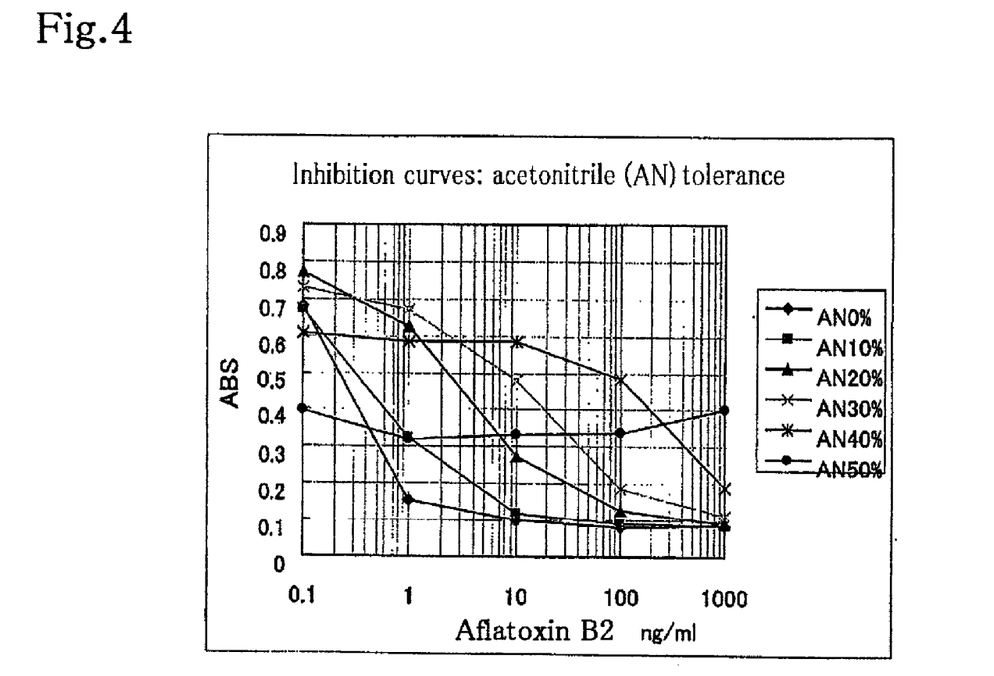
FIG. 4 shows inhibition curves of the antibody (AFB2-3-7F3-3) on aflatoxin B2 in the presence of acetonitrile in direct competitive ELISA.
Figure 5:
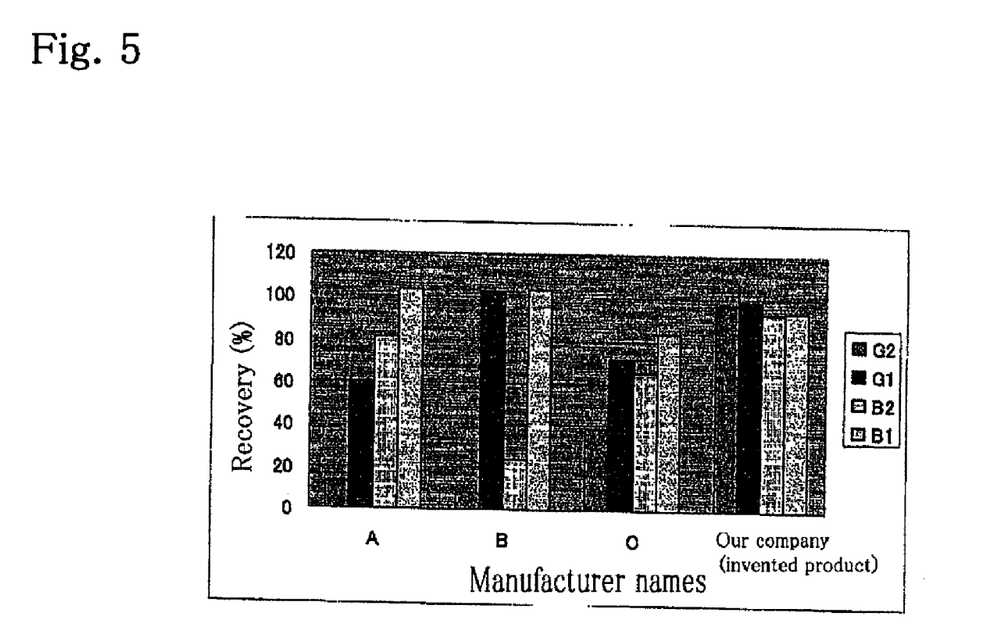
FIG. 5 shows comparison in recovery between the affinity chromatographic column (the present invention) using a gel prepared using the antibody (AFB2-3-7F3-3) and commercially available affinity chromatographic columns, where 20% acetonitrile solution containing aflatoxins B1, B2, G1 or G2 was added to each column.

On the other hand, a culture of the monoclonal antibody AFB2-3-7F3-3-producing cells was diluted 2.5-fold with 10 mM sodium phosphate buffer solution containing 0.2% BSA and 150 mM NaCl and being adjusted to pH 7.0, and added in a ratio of 19:1 to 0%, 20%, 40%, 60%, 80% and 100% methanol solutions respectively to prepare antibody dilutions.

The antibody dilution was added in a volume of 50 μL/well to the well having the same methanol concentration on the plate into which the aflatoxin B2 solutions having the predetermined concentrations had been dispensed, and the antibody was reacted by leaving it at 25° C. for 1 hour. Thereafter, the reaction was carried out as shown in (3), (4) and (5) in Example 3 to determine inhibition curves in the methanol concentrations in the reaction solutions.

The results are shown in FIG. 3. The aflatoxin antibody AFB2-3-7F3-3 showed an inhibition curve which is not disturbed even in 38% methanol, and had high tolerance to methanol. When aflatoxins present in foods are extracted, methanol is a very excellent solvent to be generally used, and it is shown that AFB2-3-7F3-3 having high tolerance to methanol is extremely useful as an antibody for detection of aflatoxins.

Example 7

Acetonitrile Tolerance of the Antibody

The acetonitrile tolerance of the monoclonal antibody AFB2-3-7F3-3 was examined. 0%, 20%, 40%, 60%, 80% and 100% aqueous acetonitrile solutions were prepared, and 0, 10, 25, 50, 100, 250, 500 and 1000 ng/ml standard solutions of aflatoxin B2 were added at 1% to the aqueous acetonitrile solutions each having the predetermined concentration, to prepare solutions containing aflatoxin B2 at a concentration of 0, 0.1, 0.25, 0.5, 1.0, 2.5, 5.0 and 10.0 ng/ml, respectively. The solution containing acetonitrile at each concentration and aflatoxin B2 at each concentration was added in a volume of 50 μL/well to the plate on which the conjugate between the aflatoxin hapten and BSA prepared in (1) in Example 3 had been solid-phased.

On the other hand, a culture of the monoclonal antibody AFB2-3-7F3-3-producing cells was diluted 50-fold with 10 mM sodium phosphate buffer solution containing 0.2% BSA and 150 mM NaCl and being adjusted to pH 7.0, and dispensed in a volume of 50 μl/well to each well of the previous plate. The antibody was reacted by leaving it at 25° C. for 1 hour, and thereafter, the reaction was carried out as shown in (3), (4) and (5) in Example 3 to determine inhibition curves in 0%, 10%, 20%, 30%, 40% and 50% acetonitrile concentrations in the reaction solutions.

The results are shown in FIG. 4. The aflatoxin antibody AFB2-3-7F3-3 showed an inhibition curve which is not disturbed even in 20% acetonitrile, and had high tolerance to acetonitrile. When aflatoxins present in foods are extracted, acetonitrile is a very excellent solvent to be generally used, and it is shown that AFB2-3-7F3-3 having high tolerance to acetonitrile is extremely useful as an antibody for detection of aflatoxins.

Example 8

Preparation of Gel 1 mL of NHS-activated Sepharose 4FF (GE Healthcare Bio Science) was washed 3 times with 10 ml of 1 mM cold hydrochloric acid. 10 ml of the antibody obtained in Example 4 (antibody solution diluted with 10 mM sodium phosphate buffer solution containing 0.5 mg/ml antibody, 0.2% BSA and 150 mM NaCl and being adjusted to pH 7.0) was added thereto, and the gel was stirred at room temperature for 4 hours and then washed 3 times with 10 ml each of a monoethanolamine buffer solution, a sodium acetate buffer solution and a monoethanolamine buffer solution in this order. 10 ml of a monoethanolamine buffer solution was added thereto, and the gel was stirred at room temperature for 3 hours and washed 3 times with 10 ml each of a sodium acetate buffer solution, a monoethanolamine buffer solution, a sodium acetate buffer solution and a phosphate buffer solution in this order.

Example 9

Preparation of an Affinity Column for Aflatoxins

An empty column was packed with 0.2 mL of the gel prepared in Example 8 and then washed twice with 3 ml of 10 mM sodium phosphate buffer containing 150 mM NaCl.

Example 10

Experiment of Addition onto and Recovery with the Affinity Column for Aflatoxins Onto this column was added 10 ml of each of 2% acetonitrile solutions each containing aflatoxins B1, B2, G1 and G2 at 6 concentrations, that is, 5 ng, 10 ng, 25 ng, 50 ng, 100 ng and 200 ng. Then, this column was washed twice with 3 ml of 10 mM sodium phosphate buffer solution containing 150 mM NaCl and twice with 3 ml water and eluted 3 times with 1 ml of 100% acetonitrile.

Then, the resulting eluate was analyzed with HPLC, and each type of aflatoxins B1, B2, G1 and G2 in the eluate was measured. The HPLC conditions are as follows: that is, column: ODS column (4.6×150 mm, 5 μm), mobile phase: acetonitrile-methanol-0.2 M ammonium acetate buffer (pH 5.0)-water (1:3:0.5:5.5), flow rate 1.0 ml/min, column temperature 40° C., detector: fluorescence detector (excitation wavelength 360 nm, fluorescence wavelength 450 nm), injection volume: 100 μl, and a photochemical reactor (Aura Industries Inc.) was arranged between the column and the detector.

The recovery (%) is as shown in Table 1.

TABLE 1

| | Aflatoxins | | | | | |
|---|---|---|---|---|---|---|
| | 5 ng | 10 ng | 25 ng | 50 ng | 100 ng | 200 ng |
| G2 | 107 | 100 | 95 | 94 | 89 | 46 |
| G1 | 95 | 95 | 94 | 92 | 89 | 54 |
| B2 | 108 | 98 | 91 | 88 | 88 | 61 |
| B1 | 99 | 94 | 89 | 87 | 88 | 72 |

(The unit of numerical values in the table is %)

From Table 1, it was found that all types of aflatoxins B1, B2, G1 and G2 was able to be almost accurately recovered in the range of from 5 ng to 100 ng.

Example 11

The affinity column using the monoclonal antibody of the present invention, prepared in Example 10, and commercially available affinity columns for aflatoxins, were used in a comparative experiment. 10 ml each of aflatoxin standard preparations (that is, 20% acetonitrile solutions each containing 50 ng each of aflatoxins B1, B2, G1 and G2) was added to the column prepared in Example 10 and commercial columns A, B and C, respectively. Each of these columns was washed twice with 3 ml of 10 mM sodium phosphate buffer containing 150 mM NaCl and twice with 3 ml water and eluted 3 times with 1 ml of 100% acetonitrile. FIG. 5 shows the recoveries of aflatoxin types B1, B2, G1 and G2 from each column.

From FIG. 5, it can be seen that the recovery from the commercial columns varies among the aflatoxin analogs, while the recovery from the affinity column having the monoclonal antibody of the present invention immobilized thereon hardly varies among the analogs, and thus has ideal properties of concentrating and purifying all aflatoxin analogs. Moreover, a solvent containing an organic solvent at high content, such as 20% acetonitrile, can also be used in the affinity column having the monoclonal antibody of the invention immobilized thereon.

From the foregoing, the monoclonal antibody obtained in the present invention, and an affinity column capable of concentrating and purifying aflatoxins by using the antibody, can be used not only in highly accurate quantification of aflatoxins but also in quantification of the individual contents of aflatoxin analogs and the total amount of aflatoxin analogs.

Reference Example

For aflatoxin B1, an aflatoxin B1 hapten was obtained by the method for aflatoxin B2 shown in Example 1. This hapten compound was used to prepare an immunogen by the method shown in Example 2 and this immunogen was used to immunize a mouse by the method shown in Example 3. Similarly, a rabbit was also immunized. The immunogen prepared in Example 2 was dissolved at 0.4 mg/mL in PBS, mixed with an equal volume of complete adjuvant (trade name: Freund's complete adjuvant; FCA) and then emulsified, and 2 mL of the resulting emulsion was administered intracutaneously to a 2.5 to 3.0 kg female rabbit (Japanese white species). In a similar manner, the immunogen mixed with an equal volume of incomplete adjuvant (trade name: Freund's incomplete adjuvant: FICA) was administered as booster 4 times at 2-week intervals. One week after final immunization was conducted, whole blood was collected, and the antibody titer in serum was confirmed by indirect competitive ELISA to be sufficiently increased. The antibody titer in serum was confirmed by indirect competitive ELISA. The results are shown in Table 2.

TABLE 2

Ability of antiserum to bind to aflatoxin analogs

| | Immunized animal IC50 ng/ml (%) | |
|---|---|---|
| | Mouse | Rabbit |
| Aflatoxin B1 | 0.07 (2163) | 0.07 (2429) |
| Aflatoxin B2 | 1.5 (100) | 1.7 (100) |
| Aflatoxin G1 | 0.6 (250) | 0.63 (270) |
| Aflatoxin G2 | 16 (9) | 18 (9) |
| Aflatoxin M1 | 11 (14) | 14 (12) |

From the results in Table 2, it can be seen that as a result of immunization of the animal with the immunogen obtained using the derivative of aflatoxin B1 as a hapten, the resulting antiserum, whether in the mouse or the rabbit, gives a particularly high activity to bind to aflatoxin B1, gives a lower activity to bind to aflatoxin G1 than to B1, and shows an only lower activity to bind to aflatoxins G2 and M1.

Sheet copy (Attention: Original is an electronic data)

(This sheet does not construct a part of International application and not includes number of sheets of International application)

| | | |
|---|---|---|
| 0-1 | Form PCT/RO/134 (SAFE) INDICATIONS RELATING TO DEPOSITED | |
| 0-1-1 | MICROORGANISM OR OTHER BIOLOGICAL MATERIAL (PCTRule13-2) were made by right | JPO-PAS 342 |
| 0-2 | International Application Number | |
| 0-3 | Applicant's or agent's file reference | PCT07050HR |
| 1 | The indications made below relate to the deposited microorganism or other biological material referred to in the description | |
| 1-1 | Paragraph number | 0017 |
| 1-3 | Identification of Deposit | |
| 1-3-1 | Name of depositary institution | IPOD International Patent Organism Depositary National Institute of Advanced Industrial Science and Technology (IPOD) |
| 1-3-2 | Address of depositary institution | AIST Tsukuba Central 6, 1-1, Higashi 1-chome Tsukuba-shi, Ibaraki-ken 305-8566 Japan |
| 1-3-3 | Date of deposit | Nov. 5, 2007(05.11.2007) |
| 1-3-4 | Accession Number | IPOD FERM ABP-10931 |
| 1-5 | Designated States for which indications are made | All Designated States |

For Receiving Office use only

| | |
|---|---|
| 0-4 | This sheet was received with the international application (Yes/No) |
| 0-4-1 | Authorized officer |

For International Bureau use only

| | |
|---|---|
| 0-5 | The date when This sheet was received by the International Bureau |
| 0-5-1 | Authorized officer |

The invention claimed is:

1. A monoclonal antibody, which is obtained by using an antigen derived from aflatoxin B2 or derivative thereof, has an ability to equally bind to all aflatoxins B1, B2, G1, G2, and M1, and has organic solvent tolerance.

2. The monoclonal antibody according to claim 1, wherein the derivative of aflatoxin B2 is a compound having a structure represented by the following formula (1):

[Formula 1]

3. The monoclonal antibody according to claim 1, wherein the antigen derived from the derivative of aflatoxin B2 is a conjugate between the compound of the formula (1) and a high-molecular compound.

4. The monoclonal antibody according to claim 1, wherein the monoclonal antibody is AFB2-3-7F3-3.

5. A hybridoma producing the monoclonal antibody according to claim 4.

6. The hybridoma according to claim 5, which has been internationally deposited under Accession No. FERM BP-10931.

* * * * *